(12) United States Patent
Yamanaka et al.

(10) Patent No.: US 9,822,342 B2
(45) Date of Patent: Nov. 21, 2017

(54) METHOD OF EFFICIENTLY INDUCING CARDIOMYOCYTES

(71) Applicant: KYOTO UNIVERSITY, Kyoto (JP)

(72) Inventors: Shinya Yamanaka, Kyoto (JP); Yoshinori Yoshida, Kyoto (JP); Kenji Miki, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/891,251

(22) PCT Filed: May 9, 2014

(86) PCT No.: PCT/JP2014/062500
§ 371 (c)(1),
(2) Date: Nov. 13, 2015

(87) PCT Pub. No.: WO2014/185358
PCT Pub. Date: Nov. 20, 2014

(65) Prior Publication Data
US 2016/0122716 A1    May 5, 2016

(30) Foreign Application Priority Data
May 14, 2013  (JP) ................................ 2013-102375

(51) Int. Cl.
*C12N 5/077* (2010.01)
*A61K 35/34* (2015.01)

(52) U.S. Cl.
CPC ............ *C12N 5/0657* (2013.01); *A61K 35/34* (2013.01); *C12N 2500/02* (2013.01); *C12N 2501/115* (2013.01); *C12N 2501/15* (2013.01); *C12N 2501/155* (2013.01); *C12N 2501/16* (2013.01); *C12N 2501/165* (2013.01); *C12N 2501/415* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 2009/0068742 A1 | 3/2009 | Yamanaka | |
| 2010/0158872 A1 | 6/2010 | Keller et al. | |
| 2010/0279403 A1 | 11/2010 | Rajesh et al. | |
| 2011/0097799 A1* | 4/2011 | Stankewicz | C12N 5/0657 435/377 |

FOREIGN PATENT DOCUMENTS

| | | |
|---|---|---|
| JP | 2008-546413 A | 12/2008 |
| JP | 2008-546414 A | 12/2008 |
| JP | 2012-519005 A | 8/2012 |
| JP | 2013-507936 A | 3/2013 |
| WO | WO 2007/002136 A2 | 1/2007 |
| WO | WO 2007/002385 A2 | 1/2007 |
| WO | WO 2007/069666 A1 | 6/2007 |
| WO | WO 2009/118928 A1 | 10/2009 |
| WO | WO 2012/024782 A1 | 3/2012 |
| WO | WO 2012/108444 A1 | 8/2012 |

OTHER PUBLICATIONS

Bauwens, C. et al., (2005) Biotechnol. Bioeng., 90: 452-461.*
Shinozawa, T. et al., "A novel purification method of murine embryonic stem cell and human induced pluripotent stem cell derived cardiomyocytes by simple dissociation", J. Biomol. Screen. ,Jan. 2012, vol. 17: pp. 683-691.*
International Search Report for International Application No. PCT/JP2014/062500, dated Jul. 29, 2014.
Chen et al., "Small molecule-mediated disruption of Wnt-dependent signaling in tissue regeneration and cancer," *Nature Chemical Biology*, vol. 5(2), pp. 100-107 (Feb. 2009).
Dubois et al., "SIRPA is a specific cell-surface marker for isolating cardiomyocytes derived from human pluripotent stem cells," *Nature Biotechnology*, vol. 29(11), pp. 1011-1018 (2011).
Iglesias-Garcia et al., "Induced pluripotent stem cells as a new strategy for cardiac regeneration and disease modeling," *Journal of Molecular and Cellular Cardiology*, vol. 62, pp. 43-50 (2013).
Kattman et al., "Stage-Specific Optimization of Activin/Nodal and BMP Signaling Promotes Cardiac Differentiation of Mouse and Human Pluripotent Stem Cell Lines," *Cell Stem Cell*, vol. 8, pp. 228-240 (Feb. 4, 2011).
Laflamme et al., "Cardiomyocytes derived from human embryonic stem cells in pro-survival factors enhance function of infarcted rat hearts," *Nature Biotechnology*, vol. 25(9), pp. 1015-1024 (Sep. 2007).
Willems et al., "Small Molecule Inhibitors of the Wnt Pathway Potently Promote Cardiomycytes from Human Embryonic Stem Cell-Derived Mesoderm," *Circulation Research*, vol. 109, pp. 360-364 (Aug. 5, 2011).
Yan et al., "Cyclosporin-A potently induces highly cardiogenic progenitors from embryonic stem cells," *Biochemical and Biophysical Research Communications*, vol. 379, pp. 115-120 (2009).
Yang et al., "Human cardiovascular progenitor cells develop from a KDR+ embryonic-stem-cell-derived population," *Nature*, vol. 453, pp. 524-528 (May 22, 2008).
Extended European Search Report issued in corresponding European Patent Application No. 14797131.1, dated Oct. 25, 2016.
Burridge et al., "Production of De Novo Cardiomyocytes: Human Pluripotent Stem Cell Differentiation and Direct Reprogramming," *Cell Stem Cell*, vol. 10(1), pp. 16-28 (Jan. 6, 2012).
Shinozawa et al., "A Novel Purification Method of Murine Embryonic Stem Cell- and Human-Induced Pluripotent Stem Cell-Derived Cardiomyocytes by Simple Manual Dissociation," *Journal of Biomolecular Screening*, vol. 17(5), pp. 683-691 (2012).

* cited by examiner

*Primary Examiner* — Michael Burkhart
(74) *Attorney, Agent, or Firm* — Knobbe, Martens, Olson & Bear LLP

(57) ABSTRACT

The present invention provides a method for efficiently producing cardiomyocytes from pluripotent stem cells, which method comprises the steps of dissociating embryoid bodies obtained during the production process, and allowing reaggregation of the resulting cells to allow formation of embryoid bodies.

13 Claims, 7 Drawing Sheets

TNT

TNT

TNT

TNT

METHOD OF EFFICIENTLY INDUCING CARDIOMYOCYTES

CROSS-REFERENCE TO RELATED APPLICATIONS

This application is the U.S. National Phase under 35 U.S.C. §371 of International Application PCT/JP 2014/062500, filed May 9, 2014, which claims priority to JP 2013-102375, filed May 14, 2013.

TECHNICAL FIELD

The present invention relates to a method for producing cardiomyocytes from pluripotent stem cells.

BACKGROUND ART

Since cardiomyocytes lose their division potential at the time of birth and hence their regeneration is difficult, recent interest has focused on replacement therapy wherein cardiomyocytes obtained by inducing differentiation of cells having pluripotency (Patent Document 1), such as embryonic stem cells (ES cells) or induced pluripotent stem cells (iPS cells), are transplanted to a cardiac tissue damaged due to myocardial infarction, myocarditis, aging or the like. Although many methods for inducing differentiation of such pluripotent stem cells into cardiomyocytes have been reported (Patent Document 2, Patent Document 3, Non-patent Document 1, Non-patent Document 2, and Non-patent Document 3), their efficiencies of differentiation induction into cardiac muscle are insufficient for clinical application.

PRIOR ART DOCUMENTS

Patent Documents

Patent Document 1: WO 2007/069666
Patent Document 2: WO 2007/002136
Patent Document 3: WO 2009/118928

Non-Patent Documents

Non-patent Document 1: Yan P, et al, Biochem Biophys Res Commun. 379: 115-20 (2009)
Non-patent Document 2: Laflamme M A, et al, Nat Biotechnol, 25: 1015-1024 (2007)
Non-patent Document 3: Yang L et al, Nature, 453: 524-528 (2008)

SUMMARY OF THE INVENTION

An object of the present invention is to provide a robust and efficient method for inducing differentiation of cardiomyocytes from pluripotent stem cells, which method is not affected by variation of the sensitivity among different cell lines.

As a result of intensive study to solve the problem described above, the present inventors discovered for the first time that, by dissociating embryoid bodies formed during a process of cardiomyocyte induction, and allowing reaggregation of the resulting cells, cardiomyocytes can be more efficiently induced compared to the conventional methods even under the same culture conditions, thereby completing the present invention.

That is, the present invention includes the following.
[1] A method for producing cardiomyocytes from pluripotent stem cells, the method comprising the following steps (1) to (4):
  (1) a step of forming an embryoid body/bodies from pluripotent stem cells;
  (2) a step of culturing the embryoid body/bodies in a medium containing activin A, bone morphogenetic protein (BMP) 4, and basic fibroblast growth factor (bFGF);
  (3) a step of dissociating the embryoid body/bodies obtained in the step (2); and
  (4) a step of culturing the cells obtained in the step (3) in a medium containing vascular endothelial growth factor (VEGF) and a Wnt inhibitor, to allow reaggregation of the cells into an embryoid body/bodies.
[2] The method according to [1], further comprising the following step:
  (5) a step of culturing the embryoid body/bodies obtained in the step (4) in a medium containing VEGF and bFGF.
[3] The method according to [2], wherein the embryoid body/bodies is/are cultured for a period of not less than 12 days in the step (5).
[4] The method according to any one of [1] to [3], wherein the culture is carried out under hypoxic conditions in the steps (2), (4), and (5).
[5] The method according to any one of [1] to [4], wherein the embryoid body/bodies is/are cultured for a period of 1 day to 5 days in the step (2).
[6] The method according to any one of [1] to [5], wherein the cells are cultured for a period of not less than 4 days in the step (4).
[7] The method according to any one of [1] to [6], wherein the Wnt inhibitor is IWP-3 or IWP-4.
[8] The method according to any one of [1] to [7], wherein the medium used in the step (4) further contains a BMP inhibitor and/or a TGFβ inhibitor.
[9] The method according to [8], wherein the BMP inhibitor is Dorsomorphin, and the TGFβ inhibitor is SB431542.
[10] The method according to any one of [1] to [9], wherein the cardiomyocytes are human cardiomyocytes.
[11] A therapeutic agent for heart diseases, comprising cardiomyocytes produced by the method according to any one of [1] to [10].

Effect of the Invention

According to the method described in the present invention, cardiomyocytes can be efficiently induced from pluripotent stem cells, and use of the induced cardiomyocytes enables recovery of cardiac function in patients with a heart disease such as myocardial infarction or heart failure

EMBODIMENTS FOR CARRYING OUT THE INVENTION

Figure 1:
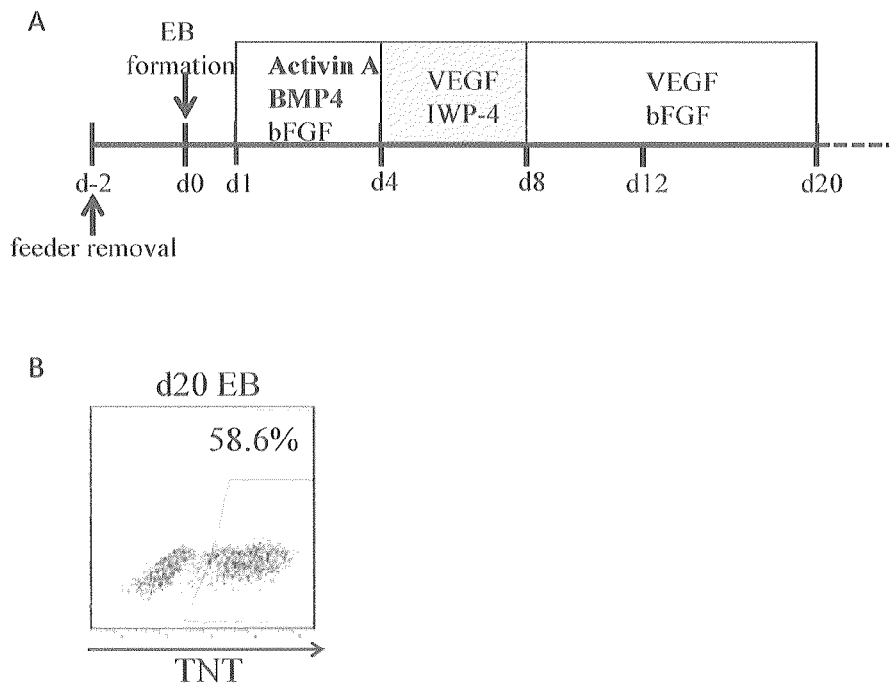
FIG. 1A shows a protocol for inducing differentiation of cardiomyocytes from pluripotent stem cells.
FIG. 1B shows the result of flow cytometric evaluation of the content of TNT-positive cells among cells obtained from iPS cells (201B7) by a conventional method.

The present invention is described below in detail.

The present invention provides a method for producing cardiomyocytes from pluripotent stem cells, which method comprises the steps of:

(1) forming an embryoid body/bodies from pluripotent stem cells;

(2) culturing the embryoid body/bodies in a medium containing activin A, BMP4, and bFGF;

(3) dissociating the embryoid body/bodies obtained in the step (2);

(4) culturing the cells obtained in the step (3) in a medium containing VEGF and a Wnt inhibitor, to allow reaggregation of the cells into an embryoid body/bodies; and, optionally, (5) culturing the embryoid body/bodies obtained in the step (4) in a medium containing VEGF and bFGF.

In the present invention, the term "cardiomyocytes" means cells of cardiac muscle having a property of autonomous beating. Unless otherwise specified, the term "cardiomyocytes" may include myocardial progenitor cells, and may also include cardiomyocytes forming beating muscle and electroconductive tissues, and cells capable of forming vascular smooth muscle. The "cardiomyocytes" may be a mixture of cardiomyocytes and myocardial progenitor cells, or may be isolated myocardial progenitor cells.

Cardiomyocytes and myocardial progenitor cells can be characterized in that they are positive for cardiac troponin (cTNT or troponin T type 2), and/or αMHC (α myosin heavy chain), which are myocardial markers. The cardiomyocytes obtained in the present invention may be a cell population containing cardiomyocytes at a higher ratio than other types of cells. The cell population preferably contains cardiomyocytes at a ratio of not less than 50%, 60%, 70%, 80%, or 90%.

<Pluripotent Stem Cells>

The pluripotent stem cells that can be used in the present invention are stem cells having pluripotency that allows differentiation into any kind of cells present in a living body, which stem cells also have the growth ability. Examples of the pluripotent stem cells include embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts or bone marrow stem cells (Muse cells). In view of obtaining stem cells without destruction of an embryo, iPS cells or Muse cells are preferably used in the present invention. Pluripotent stem cells preferably used in the method of the present invention may be cells highly applicable to the protocol of the present invention for inducing differentiation into cardiomyocytes. The term "highly applicable to the protocol of the present invention for inducing differentiation into cardiomyocytes" means that cardiomyocytes are produced with an efficiency of not less than 40%, for example, 40%, 45%, 50%, 55%, 60%, 65%, 70%, 75%, 80%, 85%, 90%, 95%, or 100%, when the differentiation induction is carried out using the cardiomyocyte differentiation induction protocol of the present invention. Pluripotent stem cells preferred in the method of the present invention may be cells having a cardiomyocyte production efficiency of not less than 70%, more preferably cells having a cardiomyocyte production efficiency of not less than 80%. The cells highly applicable to the protocol of the present invention for inducing differentiation into cardiomyocytes are not limited, and examples of the cells include cell lines of ES cells such as KhES1 and KhES3; and cell lines of iPS cells such as 201B7, 610B1, MYH, 409B2, 427F1, 606A1, 610B1, 457C1, 604A1, and 648A1. The pluripotent stem cells in the present invention may be cells having a high efficiency of induction into cardiomyocytes irrespective of the timing of the dissociation/reaggregation, or may be cells whose efficiency of induction into cardiomyocytes varies depending on the timing of the dissociation/ reaggregation. In the latter case, cells can be used as the pluripotent stem cells in the method of the present invention as long as the cells can be made to have a high efficiency of induction into cardiomyocytes by carrying out the dissociation/reaggregation at at least a certain time point during the differentiation induction process.

(A) Embryonic Stem Cells

ES cells are stem cells established from the inner cell mass of an early embryo (for example, blastocyst) of a mammal such as human or mouse, which cells have pluripotency and growth ability by self-renewal.

ES cells are embryo-derived stem cells originated from the inner cell mass of a blastocyst, which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292:154-156), and this was followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of a subject animal, followed by culturing the inner cell mass on feeder fibroblasts. The cells can be maintained by subculture using a medium supplemented with a substance(s) such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR, and 4 ng/ml bFGF at 37° C. under a moist atmosphere of 5% $CO_2$ (H. Suemori et al. (2006), Biochem. Biophys. Res. Commun., 345:926-932). ES cells need to be subcultured every 3 to 4 days, and the subculture can be carried out using 0.25% trypsin and 0.1 mg/ml collagenase IV in PBS supplemented with 1 mM $CaCl_2$ and 20% KSR.

Selection of ES cells can be generally carried out by the Real-Time PCR method using as an index/indices expression of a gene marker(s) such as alkaline phosphatase, Oct-3/4, and/or Nanog. In particular, for selection of human ES cells, expression of a gene marker(s) such as OCT-3/4, NANOG, and/or ECAD can be used as an index/indices (E. Kroon et al. (2008), Nat. Biotechnol., 26:443-452).

In terms of human ES cell lines, for example, WA01(H1) and WA09(H9) can be obtained from WiCell Research Institute, and KhES-1, KhES-2, and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF, and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors are in the form of DNA or protein. iPS cells are somatic cell-derived artificial stem cells having properties almost equivalent to those of ES cells, such as pluripotency of differentiation and growth ability by self-renewal (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, non-coding RNAs, or low molecular weight compounds, which play important roles in maintenance of the undifferentiated state of ES cells. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used individually, or two or more of these may be used in combination. Examples of the combination of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474: 225-9.

Examples of the above-described reprogramming factors also include histone deacetylase (HDAC) inhibitors [for example, low molecular weight inhibitors such as valproic acid (VPA), trichostatin A, sodium butyrate, MC 1293, and M344; and nucleic acid-type expression inhibitors such as siRNAs and shRNAs against HDAC (e.g., HDAC1 siRNA Smartpool (registered trademark) (Millipore) and HuSH 29mer shRNA Constructs against HDAC1 (OriGene))], MEK inhibitors (for example, PD184352, PD98059, U0126, SL327, and PD0325901), Glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1, and G9a), L-channel calcium agonists (for example, Bayk8644), butyric acid, TGFβ inhibitors or ALK5 inhibitors (for example, LY364947, SB431542, 616453, and A-83-01), p53 inhibitors (for example, siRNAs and shRNAs against p53), ARID3A inhibitors (for example, siRNAs and shRNAs against ARID3A), miRNAs such as miR-291-3p, miR-294, miR-295, and mir-302, Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2, and DMRTB1, which are employed for enhancing the establishment efficiency, and, in the present description, these factors employed for the purpose of enhancement of the establishment efficiency are not particularly distinguished from reprogramming factors.

In cases where the reprogramming factors are in the form of protein, the reprogramming factors may be introduced into somatic cells by a method such as lipofection, fusion with a cell membrane-permeable peptide (e.g., HIV-derived TAT or polyarginine), or microinjection.

In cases where the reprogramming factors are in the form of DNA, the reprogramming factors may be introduced into somatic cells by a method such as use of a vector including virus, plasmid, and artificial chromosome vectors; lipofection; use of liposome; or microinjection. Examples of the virus vectors include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors, and Sendai virus vectors (WO 2010/008054). Examples of the artificial chromosome vectors include human artificial chromosomes (HACs), yeast artificial chromosomes (YACs), and bacterial artificial chromosomes (BACs and PACs). Examples of the plasmids which may be used include plasmids for mammalian cells (Science, 322:949-953, 2008). The vectors may contain a regulatory sequence(s) such as a promoter, enhancer, ribosome binding sequence, terminator, and/or polyadenylation site to enable expression of the nuclear reprogramming factors; and, as required, a sequence of a selection marker such as a drug resistance gene (e.g., kanamycin-resistant gene, ampicillin-resistant gene, or puromycin-resistant gene), thymidine kinase gene, or diphtheria toxin gene; a gene sequence of a reporter such as the green-fluorescent protein (GFP), β-glucuronidase (GUS), or FLAG; and/or the like. Further, in order to remove, after introduction of the above vector into somatic cells, the genes encoding the reprogramming factors, or both the promoters and the genes encoding the reprogramming factors linked thereto, the vector may have LoxP sequences upstream and downstream of these sequences.

In cases where the reprogramming factors are in the form of RNA, each reprogramming factor may be introduced into somatic cells by a method such as lipofection or microinjection, and an RNA in which 5-methylcytidine and pseudouridine (TriLink Biotechnologies) are incorporated may be used in order to suppress degradation (Warren L, (2010) Cell Stem Cell. 7:618-630).

Examples of the medium for induction of the iPS cells include DMEM, DMEM/F12, and DME media supplemented with 10 to 15% FBS (these media may further contain LIF, penicillin/streptomycin, puromycin, L-glutamine, non-essential amino acids, β-mercaptoethanol, and/or the like, as appropriate); and commercially available media [for example, a medium for culturing mouse ES cells (TX-WES medium, Thromb-X), medium for culturing primate ES cells (medium for primate ES/iPS cells, ReproCELL), and serum-free medium (mTeSR, Stemcell Technology)].

Examples of the culture method include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in the DMEM medium supplemented with 10% FBS (this medium may further contain LIF, penicillin/streptomycin, puromycin, L-glutamine, non-essential amino acids, β-mercaptoethanol, and/or the like, as appropriate) for about 25 to about 30 days or longer, to allow ES-like colonies to appear. Preferred examples of the culture method include a method wherein the somatic cells themselves to be reprogrammed are used instead of the feeder cells (Takahashi K, et al. (2009), PLoS One. 4:e8067; or WO 2010/137746), and a method wherein an extracellular matrix (e.g., Laminin-5 (WO 2009/123349) or Matrigel (BD)) is used instead.

Other examples of the culture method include a method wherein culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of 0.1% to 15%) (Yoshida Y, et al. (2009), Cell Stem Cell. 5:237-241 or WO2010/013845).

During the culture, the medium is replaced with fresh medium once every day from Day 2 of the culture. The number of the somatic cells to be used for nuclear reprogramming is not restricted, and usually within the range of about $5\times10^3$ to about $5\times10^6$ cells per 100-cm² area on the culture dish.

iPS cells may be selected based on the shape of each formed colony. In cases where a drug resistance gene to be expressed in conjunction with a gene expressed in reprogrammed somatic cells (e.g., Oct3/4 or Nanog) is introduced as a marker gene, established iPS cells can be selected by culturing the cells in a medium containing the corresponding drug (selection medium). Further, iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" to be used in the present description means any animal cells (preferably cells of mammals including human) excluding germ-line cells and totipotent cells such as eggs, oocytes, and ES cells. Examples of the somatic cells include, but are not limited to, any of fetal somatic cells, neonatal somatic cells, and healthy or diseased mature somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

In cases where iPS cells are used as a material for cells to be transplanted, somatic cells whose HLA genotype is the same or substantially the same as that of the individual to which the cells are to be transplanted are preferably used in view of prevention of the rejection reaction. The term "substantially the same" herein means that the HLA genotype is matching to an extent at which the immune reaction against the transplanted cells can be suppressed with an immunosuppressive agent. For example, the somatic cells have matched HLA types at the 3 loci HLA-A, HLA-B, and HLA-DR, or at the 4 loci further including HLA-C.

(E) ES Cells Derived from Cloned Embryo Obtained by Nuclear Transfer ntES cells are ES cells derived from a cloned embryo prepared by the nuclear transfer technique, and have almost the same properties as those of ES cells derived from fertilized eggs (T. Wakayama et al. (2001), Science, 292: 740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique is employed (Sayaka Wakayama et al. (2008), Experimental Medicine 26(5) (extra edition), pp. 47-52). In nuclear transfer, reprogramming can be achieved by injecting the nucleus of a somatic cell into a mammalian enucleated unfertilized egg and culturing the resultant for several hours.

(F) Multilineage-Differentiating Stress Enduring Cells (Muse Cells)

Muse cells are pluripotent stem cells produced by the method described in WO 2011/007900. More specifically, Muse cells are cells having pluripotency obtained by subjecting fibroblasts or bone marrow stromal cells to trypsin treatment for a long period, preferably to trypsin treatment for 8 hours or 16 hours, followed by suspension culture of the treated cells. Muse cells are positive for SSEA-3 and CD105.

<Step of Forming Embryoid Bodies from Pluripotent Stem Cells: Step (1)>

Preferably, in this step, pluripotent stem cells forming colonies are dissociated into single cells, and then allowed to form embryoid bodies. In the step of dissociating the pluripotent cells, cells adhering to each other and forming populations are dissociated (separated) into individual cells. Examples of the method for dissociating the pluripotent stem cells include a method in which the cells are mechanically dissociated, and a method in which a dissociation solution having protease activity and collagenase activity (e.g., Accutase™ or Accumax™) or a dissociation solution having only collagenase activity is used. The method is preferably a method in which a dissociation solution having protease activity and collagenase activity (especially preferably Accumax) is used to dissociate the pluripotent stem cells.

In the method of the present invention, examples of the method for forming the embryoid bodies include subjecting the dissociated pluripotent stem cells to suspension culture using a culture dish whose surface is not artificially treated for the purpose of improving adhesion of cells thereto (for example, not subjected to coating treatment with Matrigel (BD), collagen, gelatin, laminin, heparan sulfate proteoglycan, or entactin) or using a culture dish which is artificially treated such that the adhesion is suppressed (for example, treated by coating with polyhydroxyethyl methacrylate (poly-HEMA)). In the method of the present invention, the number of pluripotent stem cells used for forming the embryoid bodies for the purpose of inducing cardiomyocytes is preferably 1000 to 4000, more preferably 2000 to 4000.

<Step of Culturing Embryoid Bodies in Medium Containing Activin A, BMP4, and bFGF: Step (2)>

The medium to be used in this step can be prepared using a medium for animal cell culture as a basal medium, and adding activin A, BMP4, and bFGF thereto. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and StemPro34 (Invitrogen), and mixtures of two or more of these media. The medium may contain serum, or may be serum-free. If necessary, the medium may contain one or more of serum replacements such as albumin, transferrin, Knockout Serum Replacement (KSR) (serum replacement for FBS in ES cell culture), N2 supplement (Invitrogen), B27 supplement (Invitrogen), fatty acids, insulin, collagen precursor, trace elements, 2-mercaptoethanol, and 1-thiolglycerol, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, and inorganic salts. A preferred basal medium is StemPro34, which contains transferrin, 1-thiolglycerol, L-glutamine, and ascorbic acid.

The concentration of activin A to be used in the present step is preferably 1 ng/ml to 100 ng/ml. Examples of the concentration of activin A include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. The concentration of activin A is especially preferably 12 ng/ml.

The concentration of BMP4 to be used in the present step is preferably 1 ng/ml to 100 ng/ml. Examples of the concentration of BMP4 include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. The concentration of BMP4 is especially preferably 18 ng/ml.

The concentration of bFGF to be used in the present step is preferably 1 ng/ml to 100 ng/ml. Examples of the concentration of bFGF include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. The concentration of bFGF is especially preferably 10 ng/ml.

In terms of culture conditions, the culture temperature is about 30 to 40° C., preferably about 37° C., although the culture temperature is not limited thereto. The culture is preferably carried out under hypoxic conditions. The term "hypoxic conditions" herein means conditions where the oxygen partial pressure is lower than the oxygen partial pressure in the air (20%). For example, the oxygen partial pressure is from 1% to 15%, and examples of the oxygen partial pressure include 10%, 9%, 8%, 7%, 6%, 5%, 4%, 3%, 2%, and 1%. The oxygen partial pressure is more preferably 5%. The culture is carried out under an atmosphere of air containing $CO_2$, and the $CO_2$ concentration is preferably about 2 to 5%.

The culture period is, for example, from 1 day to 7 days. Considering the establishment efficiency of cardiomyocytes, examples of the culture period include periods of from 1 day to 5 days, periods of from 1.5 days to 5 days, and periods of from 2 days to 4 days. The culture period in the present invention may be, for example, 1 day, 1.5 days, 2 days, 2.5 days, 3 days, 3.5 days, 4 days, 4.5 days, 5 days, 5.5 days, 6 days, 6.5 days, or 7 days. The culture period may be preferably 2 days.

<Step of Dissociating Embryoid Bodies During Production Process: Step (3)>

In the present invention, the method for dissociating the embryoid bodies may be the same as the method described for the step (1).

<Step of Culturing in Medium Containing VEGF and Wnt Inhibitor to Allow Formation of Embryoid Bodies by Reaggregation: Step (4)>

In the formation of embryoid bodies by reaggregation, the number of cells to be used is not limited as long as the cells adhere to each other to allow preparation of cell clusters. Examples of the number of the cells include, but are not limited to, 1000 to 20,000. A preferred example of the number of cells is 10,000. As described for the step (1), the culture is preferably suspension culture using a culture vessel whose surface is not artificially treated for the purpose of improving adhesion of cells thereto, or using a culture vessel which is artificially treated such that the adhesion is suppressed.

The medium to be used in this step can be prepared using a medium for animal cell culture as a basal medium, and adding VEGF and a Wnt inhibitor thereto. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and StemPro34 (Invitrogen), and mixtures of two or more of these media. The medium may contain serum, or may be serum-free. If necessary, the medium may contain one or more of serum replacements such as albumin, transferrin, Knockout Serum Replacement (KSR) (serum replacement for FBS in ES cell culture), N2 supplement (Invitrogen), B27 supplement (Invitrogen), fatty acids, insulin, collagen precursor, trace elements, 2-mercaptoethanol, and 1-thiolglycerol, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, and inorganic salts. A preferred basal medium is StemPro34, which contains transferrin, 1-thiolglycerol, L-glutamine, and ascorbic acid.

In the present invention, the Wnt inhibitor is a substance that inhibits the signaling pathway from binding of Wnt to its receptor to accumulation of β-catenin. The Wnt inhibitor is not limited as long as it is a substance that inhibits binding of Wnt to the receptor, Frizzled family, or a substance that promotes degradation of β-catenin. Examples of the Wnt inhibitor include DKK1 protein (for example, in human, NCBI accession No. NM_012242), sclerostin (for example, in human, NCBI accession No. NM_025237), IWR-1 (Merck Millipore), IWP-2 (Sigma-Aldrich), IWP-3 (Sigma-Aldrich), IWP-4 (Sigma-Aldrich), PNU-74654 (Sigma-Aldrich), and XAV939 (Sigma-Aldrich), and their derivatives.

The TGFβ inhibitor to be used in this step may be preferably IWP-3 or IWP-4.

The concentration of the Wnt inhibitor such as IWP-3 or IWP-4 in the medium is not limited as long as inhibition of Wnt occurs. The concentration of the Wnt inhibitor is preferably 1 nM to 50 μM. Examples of the concentration of the Wnt inhibitor include, but are not limited to, 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration of the Wnt inhibitor is preferably 1 μM.

The concentration of VEGF to be used in this step is preferably 1 to 100 ng/ml. Examples of the concentration of VEGF include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. The concentration of VEGF is more preferably 10 ng/ml.

In this step, a BMP inhibitor and/or a TGFβ inhibitor may be further added to the basal medium.

In the present invention, examples of the BMP inhibitor include inhibitor proteins such as Chordin, Noggin, and Follistatin; Dorsomorphin (that is, 6-[4-(2-piperidin-1-yl-ethoxy)phenyl]-3-pyridin-4-yl-pyrazolo[1,5-a]pyrimidine), its derivatives (P. B. Yu et al. (2007), Circulation, 116:II_60; P. B. Yu et al. (2008), Nat. Chem. Biol., 4:33-41; J. Hao et al. (2008), PLoS ONE, 3(8):e2904), and LDN-193189 (that is, 4-(6-(4-(piperazin-1-yl)phenyl)pyrazolo[1,5-a]pyrimidin-3-yl)quinoline). Dorsomorphin and LDN-193189 are commercially available, and can be obtained from Sigma-Aldrich and Stemgent, respectively.

The BMP inhibitor to be used in this step may be preferably Dorsomorphin.

The concentration of the BMP inhibitor such as Dorsomorphin in the medium is not limited as long as inhibition of BMP occurs at the concentration. The concentration of the BMP inhibitor is preferably 1 nM to 50 μM. Examples of the concentration of the BMP inhibitor include, but are not limited to, 1 nM, 10 nM, 50 nM, 100 nM, 500 nM, 600 nM, 700 nM, 800 nM, 900 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration of the BMP inhibitor is more preferably 600 nM.

In the present invention, the TGFβ inhibitor is a substance that inhibits the signaling pathway from binding of TGFβ to its receptor to SMAD. The TGFβ inhibitor is not limited as long as it is a substance that inhibits the binding of TGFβ to the receptor, ALK family, or a substance that inhibits phosphorylation of SMAD by the ALK family. Examples of the TGFβ inhibitor include Lefty-1 (for example, NCBI Accession Nos. NM_010094 (mouse) and NM_020997 (human)), SB431542, SB202190 (these are described in R. K. Lindemann et al., Mol. Cancer, 2003, 2:20), SB505124 (GlaxoSmithKline), NPC30345, SD093, SD908, SD208 (Scios), LY2109761, LY364947, LY580276 (Lilly Research Laboratories), and A-83-01 (WO 2009146408), and their derivatives.

The TGFβ inhibitor to be used in this step may be preferably SB431542.

The concentration of the TGFβ inhibitor such as SB431542 in the medium is not limited as long as inhibition of ALKS occurs at the concentration. The concentration of the TGFβ inhibitor is preferably 1 nM to 50 μM. Examples of the concentration of the TGFβ inhibitor include, but are not limited to, 1 nM, 10 nM, 50 nM, 100 nM, 500 nM, 750 nM, 1 μM, 2 μM, 3 μM, 4 μM, 5 μM, 5.2 μM, 5.4 μM, 5.6 μM, 5.8 μM, 6 μM, 7 μM, 8 μM, 9 μM, 10 μM, 15 μM, 20 μM, 25 μM, 30 μM, 40 μM, and 50 μM. The concentration of the TGFβ inhibitor is more preferably 5.4 μm.

In terms of culture conditions, the culture temperature is about 30 to 40° C., preferably about 37° C., although the culture temperature is not limited thereto. The culture is preferably carried out under hypoxic conditions. The term "hypoxic conditions" herein means conditions where the oxygen partial pressure is lower than the oxygen partial pressure in the air (20%). For example, the oxygen partial pressure is from 1% to 15%, and examples of the oxygen partial pressure include 10%, 9%, 8%, 7%, 6%, 5%, 4%, 3%, 2%, and 1%. The oxygen partial pressure is more preferably 5%. The culture is carried out under an atmosphere of air containing $CO_2$, and the $CO_2$ concentration is preferably about 2 to 5%.

The upper limit of the culture period is not specified since long-term culture does not influence the establishment of cardiomyocytes. The culture is preferably carried out for not less than 4 days. Examples of the culture period include 4 days, 5 days, 6 days, 7 days, 8 days, 9 days, and 10 days. This allows the embryoid bodies formed by reaggregation to differentiate into cardiomyocytes.

<Step of Culturing in Medium Containing VEGF and bFGF: Step (5)>

The medium to be used in this step can be prepared using a medium for animal cell culture as a basal medium, and adding VEGF and bFGF thereto. Examples of the basal medium include IMDM, Medium 199, Eagle's Minimum Essential Medium (EMEM), αMEM, Dulbecco's modified Eagle's Medium (DMEM), Ham's F12 medium, RPMI 1640 medium, Fischer's medium, Neurobasal Medium (Life Technologies), and StemPro34 (Invitrogen), and mixtures of two or more of these media. The medium may contain serum, or may be serum-free. If necessary, the medium may contain one or more of serum replacements such as albumin, transferrin, Knockout Serum Replacement (KSR) (serum replacement for FBS in ES cell culture), N2 supplement (Invitrogen), B27 supplement (Invitrogen), fatty acids, insulin, collagen precursor, trace elements, 2-mercaptoethanol, and 1-thiolglycerol, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, and inorganic salts. A preferred basal medium is StemPro34, which contains transferrin, 1-thiolglycerol, L-glutamine, and ascorbic acid.

The concentration of VEGF to be used in this step is preferably 1 to 100 ng/ml. Examples of the concentration of VEGF include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. The concentration of VEGF is more preferably 10 ng/ml.

The concentration of bFGF to be used in this step is preferably 1 to 100 ng/ml. Examples of the concentration of bFGF include 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml, 19 ng/ml, 20 ng/ml, 30 ng/ml, 40 ng/ml, 50 ng/ml, 60 ng/ml, 70 ng/ml, 80 ng/ml, 90 ng/ml, and 100 ng/ml. The concentration of bFGF is more preferably 5 ng/ml.

In terms of culture conditions, the culture temperature is about 30 to 40° C., preferably about 37° C., although the culture temperature is not limited thereto. The culture is preferably carried out under hypoxic conditions. The term "hypoxic conditions" herein means conditions where the oxygen partial pressure is lower than the oxygen partial pressure in the air (20%). For example, the oxygen partial pressure is from 1% to 15%, and examples of the oxygen partial pressure include 10%, 9%, 8%, 7%, 6%, 5%, 4%, 3%, 2%, and 1%. The oxygen partial pressure is more preferably 5%. In the middle of this step, the oxygen partial pressure may be equivalent to that in the air. Since culturing under hypoxic conditions does not influence the efficiency of induction of cardiomyocytes in such cases, the upper limit is not specified, but the culture under hypoxic conditions is preferably carried out for not less than 4 days in the early phase of this step. The culture is carried out under an atmosphere of air containing $CO_2$, and the $CO_2$ concentration is preferably about 2 to 5%.

The upper limit of the culture period is not specified since long-term culture does not influence the establishment of cardiomyocytes. The culture is preferably carried out for not less than 12 days. Examples of the culture period include 8 days, 9 days, 10 days, 11 days, 12 days, 13 days, 14 days, 15 days, 16 days, 17 days, 18 days, 19 days, 20 days, 21 days, and 22 days, and periods longer than these. By further subjecting the cells obtained in the step (4) to culture according to the step (5), the efficiency of differentiation into cardiomyocytes can be increased.

<Therapeutic Agent for Heart Diseases>

The cardiomyocytes obtained by the present invention can be used as a therapeutic agent for heart diseases in animals (preferably human). The therapeutic method for heart diseases may be carried out by suspending the obtained cardiomyocytes in physiological saline or the like and administering the cells directly to the myocardium of the heart of the patient, or by preparing a sheet from the obtained cardiomyocytes and attaching the sheet to the heart of the patient. In the former case, the cells alone may be administered, or the cells may be administered together with a scaffold material that promotes their survival. Examples of the scaffold material herein include, but are not limited to, tissue-derived components such as collagen; and synthetic polymers as alternatives to these components, such as polylactic acid. In cases where a cardiomyocyte sheet is administered, the administration is achieved by placing the sheet such that the sheet covers the desired area. Here, a technique well known in the art may be used for placing the sheet such that the sheet covers the desired area. In cases where the size of the desired area is large, the placement may be carried out such that the tissue is surrounded by the sheet. In the administration, the placement on the area may be carried out several times for obtaining a desired effect. In cases where the placement is carried out several times, these operations of placement are preferably carried out at sufficient time intervals so that the desired cells survive on the tissue to allow angiogenesis. The mechanism of the treatment of heart diseases may be an effect produced by survival of the cardiomyocyte sheet, or may be an indirect action independent of survival of the cells (for example, an effect by secretion of an attractant which causes recruitment of recipient-derived cells to the damaged area). In cases where a cardiomyocyte sheet is used for treatment of a heart disease, a cell scaffold material (scaffold) such as collagen, fibronectin, or laminin may be contained in addition to the cardiomyocytes. Further, the cardiomyocyte sheet may contain an arbitrary type (or a plurality of arbitrary types) of cells in addition to the cardiomyocytes. Examples of the heart diseases which can be treated in the present invention include, but are not limited to, defects due to diseases and disorders such as heart failure, ischemic heart diseases, myocardial infarction, cardiomyopathy, myocarditis, hypertrophic cardiomyopathy, dilated phase of hypertrophic cardiomyopathy, and dilated cardiomyopathy.

In the present invention, the number of cardiomyocytes to be used for the treatment of a heart disease is not limited as long as the cardiomyocytes or the cardiomyocyte sheet administered can produce an effect in the treatment the heart disease. The number of cardiomyocytes may be increased or decreased depending on the size of the affected area and/or the body size, if necessary.

EXAMPLES

The present invention is described below more concretely by way of Examples. However, needless to say, the present invention is not limited to these.
Pluripotent Stem Cells
The following cell lines were used.
(1) 201B7 Cell Line
This cell line was prepared by the method described in Takahashi K, et al. Cell. 131: 861-72, 2007.
(2) 610B1 Cell Line
According to the method described in Okita. K, et al., Stem Cells. 2012 Nov. 29, the iPS cell line was prepared by transfecting human umbilical cord blood (obtained from RIKEN BRC) with episomal vectors (pCXLE-hOCT3/4-shp53-F, pCXLE-hSK, and pCXLE-hUL) by electroporation, and culturing the transfected cells on mouse fetal fibroblast feeders treated with mitomycin. The culture was carried out by a conventional method (Takahashi K, et al. Cell. 131: 861-72, 2007; and Nakagawa M, et al. Nat Biotechnol. 26: 101-6, 2008).
(3) MYH Cell Line
This cell line was prepared by introducing a vector in which an EGFP cassette is operably linked downstream of an MYH (myosin heavy chain) 6 promoter, into the 201B7 cell line using the PiggyBac transposon system (System Biosciences, Inc.). The culture was carried out by the same method as described above.
(4) 409B2 Cell Line
This cell line was prepared by introducing pCXLE-hOCT3/4-shp53-F, pCXLE-hSK, and pCXLE-hUL into HDF1388 according to the method described in Okita et al., Nat Methods. 8(5):409-12. (2011). The culture was carried out by the same method as described above.
(5) 427F1 Cell Line
This cell line was prepared by introducing pCXLE-hOCT3/4-shp53-F, pCXLE-hSK, and pCXLE-hUL to HDF-1437. The culture was carried out by the same method as described above.
(6) 606A1 Cell Line
This cell line was prepared by introducing pCXLE-hOCT3/4-shp53-F, pCXLE-hSK, and pCXLE-hUL to CB CD34#1 according to the method described in Okita et al., Stem Cells. 31(3):458-66 (2013). The culture was carried out by the same method as described above.
(7) 610B1 Cell Line
This cell line was prepared by introducing pCXLE-hOCT3/4-shp53-F, pCXLE-hSK, and pCXLE-hUL to CB CD34#2 according to the method described in Okita et al., Stem Cells. 31(3):458-66 (2013). The culture was carried out by the same method as described above.
(8) 457C1 Cell Line
This cell line was prepared by introducing pCXLE-hOCT3/4-shp53-F, pCXLE-hSK, and pCXLE-hUL to DP74 according to the method described in Okita et al., Nat Methods. 8(5):409-12 (2011). The culture was carried out by the same method as described above.
(9) 604A1 Cell Line
This cell line was prepared by introducing pCXLE-hOCT3/4-shp53-F, pCXLE-hSK, and pCXLE-hUL to PBMNαβT according to the method described in Kajiwara et al. Proc Natl Acad Sci USA. 109(31):12538-43 (2012). The culture was carried out by the same method as described above.
(10) 648A1 Cell Line
This cell line was prepared by introducing pCXLE-hOCT3/4-shp53-F, pCXLE-hSK, and pCXLE-hUL to PBMN #2 non-T, non-B according to the method described in Okita et al., Stem Cells. 31(3):458-66 (2013). The culture was carried out by the same method as described above.
(11) KhES1 Cell Line and KhES3 Cell Line
As human ES cells, the KhES1 cell line and the KhES3 cell line, established by Stem Cell Research Center, Institute for Frontier Medical Sciences, Kyoto University, were used. The culture was carried out by a conventional method (Suemori H, et al. Biochem Biophys Res Commun. 345: 926-32, 2006).
Method for Inducing Cardiomyoctes (Comparative Example: FIG. 1A)

Three days before differentiation induction (Day −3), the 201B7 cell line was treated with Collagenase type B solution (Roche) for 5 minutes, and the solution was then removed, followed by treating the cells with 0.25% trypsin-EDTA (Invitrogen) for 2 to 3 minutes. After washing the cells with PBS solution (Nacalai Tesque), the obtained iPS cells were detached with a cell scraper and recovered. The iPS cells were then plated on a well of a Matrigel-coated 6-well plate, and cultured in MEF (mouse fetal fibroblast)-conditioned medium (MEF-CM) for 3 days.

Subsequently (Day 0), treatment with Collagenase type B solution was carried out for 10 minutes. After removing the solution, the iPS cells were treated with 0.25% trypsin-EDTA for 1 to 2 minutes, and then detached with a cell scraper. STEMPRO 34 (Invitrogen) supplemented with 1% L-glutamine (Invitrogen), 150 μg/mL transferrin (Roche), 50 μg/mL ascorbic acid (Sigma), $3.9 \times 10^{-3}$% MTG (1-Thyoglycerol) (Sigma), 10 μM Rock inhibitor (Y-27632, Wako), and 2 ng/mL BMP4 (R&D) was added to the cells, and the cells were then divided into small clusters by pipetting. The resulting cell clusters were transferred to a well of a low-adhesion E-well plate, and culture was carried out at 37° C. under 5% oxygen to prepare embryoid bodies (EBs).

On the next day (Day 1), the EBs were recovered by centrifugation, and transferred to 4 wells of a low-adhesion 24-well plate. Thereafter, culture was carried out for 3 days at 37° C. under 5% oxygen in STEMPRO 34 supplemented with 1% L-glutamine, 150 μg/mL transferrin, 50 μg/mL ascorbic acid, $3.9 \times 10^{-3}$% MTG, 10 ng/mL BMP4, 5 ng/mL bFGF (R&D), and 6 ng/mL activin A (R&D).

Subsequently (Day 4), after removal of the medium, culture was carried out for 4 days at 37° C. under 5% oxygen in STEMPRO 34 supplemented with 1% L-glutamine, 150 μg/mL transferrin, 50 μg/mL ascorbic acid, $3.9 \times 10^{-3}$% MTG, 10 ng/mL VEGF (R&D), and 1 μM IWP-3 (Stemolecule).

Subsequently (Day 8), after removal of the medium, culture was carried out for 4 days at 37° C. under 5% oxygen in STEMPRO 34 supplemented with 1% L-glutamine, 150 μg/mL transferrin, 50 μg/mL ascorbic acid, $3.9 \times 10^{-3}$% MTG, 10 ng/mL VEGF, and 5 ng/mL bFGF. During this culture, the medium was replaced every other day with the same fresh medium.

Subsequently (Day 12), the plate was transferred to an incubator with normal oxygen concentration, and culture was carried out for 8 days. During this culture, the medium was replaced every other day with the same fresh medium.

After the culture (Day 20), the obtained cells were evaluated. As a result, the content of cTNT-positive cells was 58.6% (FIG. 1B). From about Day 8, beating was found.

Similar results were obtained in a case where IWP-4 was used instead of IWP-3 on Day 4.

Example 1

Modified Method for Inducing Cardiomyocytes

After treatment of the 201B7 cell line with CTK solution (ReproCELL) for 2 minutes, the solution was removed. Subsequently, the cells were treated with Accumax (Innovative Cell Technologies) for 5 minutes, and dissociated into single cells by pipetting. The cells were recovered by centrifugation, and plated on a low-adhesion 96-well dish (Corning) at 2500 cells/well. Culture was carried out at 37° C. under 5% oxygen in STEMPRO 34 supplemented with 1% L-glutamine, 150 μg/mL transferrin, 50 μg/mL ascorbic acid (Sigma), $3.9 \times 10^{-3}$% MTG, 10 μM Rock inhibitor, 2 ng/mL BMP4 (R&D), and 0.50% Matrigel (Growth Factor Reduced), to allow formation of EBs (Day 0). It was found, in this culture, that the efficiency of induction of cardiomyocytes decreases in cases where the EB cells are formed from not more than 1000 cells or not less than 4000 cells per well.

On the next day (Day 1), an equal volume of STEMPRO 34 supplemented with 1% L-glutamine, 150 μg/mL transferrin, 50 μg/mL ascorbic acid, $3.9 \times 10^{-3}$% MTG, 18 ng/mL BMP4, 10 ng/mL bFGF, and 12 ng/mL activin A was added to the 96-well plate in which the EBs were cultured, and culture was carried out at 37° C. under 5% oxygen for 3 days.

Subsequently (Day 4), the obtained EBs were allowed to naturally precipitate, and the medium was removed. Accumax was added to the EBs, and, 5 minutes later, the EBs were dissociated into single cells by pipetting. After addition of 5 ml of IMDM (Invitrogen), the medium was removed by centrifugation. The cells were plated on a low-adhesion 96-well plate (Corning) at 10,000 cells/well, and cultured at 37° C. under 5% oxygen for 4 days in STEMPRO 34 supplemented with 1% L-glutamine, 150 μg/mL transferrin, 50 μg/mL ascorbic acid, $3.9 \times 10^{-3}$% MTG, 10 ng/mL VEGF, and 1 μM IWP-3.

Subsequently (Day 8), the obtained EBs were recovered, and transferred to a 24-well dish such that the number of EBs did not exceed 10 EBs per well. Culture was carried out for 4 days at 37° C. under 5% oxygen in STEMPRO 34 supplemented with 1% L-glutamine, 150 μg/mL transferrin, 50 μg/mL ascorbic acid, $3.9 \times 10^{-3}$% MTG, 10 ng/mL VEGF, and 5 ng/mL bFGF. During this culture, the medium was replaced every other day with the same fresh medium.

Subsequently (Day 12), the dish was transferred to an incubator with normal oxygen concentration, and culture was carried out for 8 days. During this culture, the medium was replaced every other day with the same fresh medium.

Figure 2:
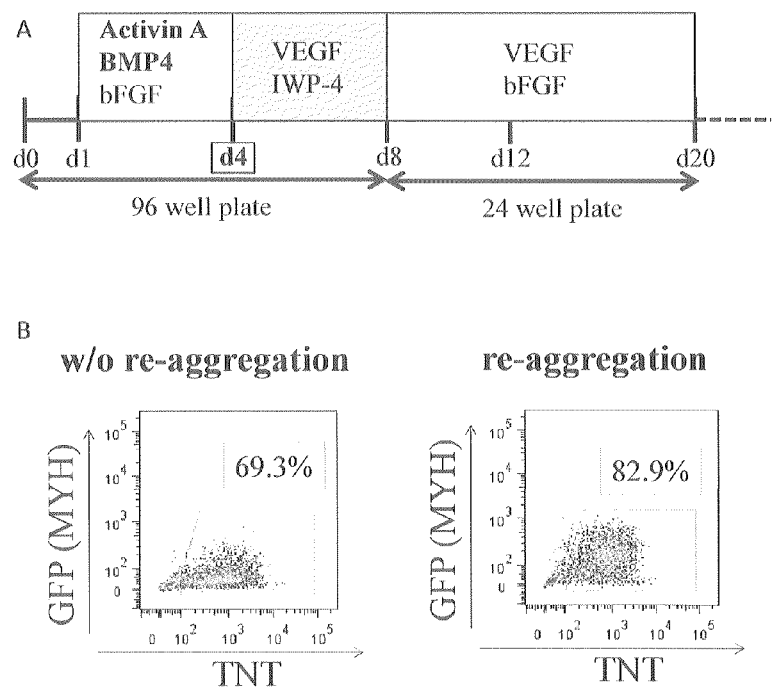
FIG. 2A shows a modified protocol for inducing differentiation of cardiomyocytes from pluripotent stem cells.
FIG. 2B shows the results obtained by the novel protocol in which the dissociation/reaggregation was carried out (right panel) or not carried out (left panel) on Day 4, wherein the content of TNT-positive cells among the obtained cells was evaluated by flow cytometry.

After the culture (Day 20), the obtained cells were evaluated. As a result, the content of cTNT-positive cells was 82.9% (FIG. 2B, right panel).

Similar results were obtained in a case where IWP-4 was used instead of IWP-3 on Day 4. Similar results were also obtained in a case where 5.4 μM SB431542 (Sigma) and 0.6 μM Dorsomorphin (Sigma) were added to the medium on Day 4.

On the other hand, culture was carried out in the same manner except that the dissociation into single cells on Day 4 was not carried out, while the replacement of the medium to STEMPRO 34 supplemented with 1% L-glutamine, 150 μg/mL transferrin, 50 μg/mL ascorbic acid, $3.9 \times 10^{-3}$% MTG, 10 ng/mL VEGF, and 1 μM IWP-3 was carried out. As a result, the content of cTNT-positive cells on Day 20 was 69.3% (FIG. 2B, left panel). Thus, it was confirmed that the dissociation into single cells on Day 4 increases the efficiency of induction of cardiomyocytes.

Example 2

Study of Timing of Dissociation/Reaggregation of EBs (1)

In the modified method for inducing cardiomyocytes in Example 1, the timing of the dissociation into single cells carried out on Day 4 followed by the reaggregation was changed to investigate the effect of the change on pluripotent stem cell lines (201B7 cell line, 610B1 cell line, and 409B2-2 cell line; and KhES1 cell line) (FIGS. 3 to 6). The culture in STEMPRO 34 supplemented with 1% L-glutamine, 150 μg/mL transferrin, 50 μg/mL ascorbic acid, $3.9 \times 10^{-3}$% MTG, 18 ng/mL BMP4, 10 ng/mL bFGF, and 12 ng/mL activin A, which is started on Day 1, was carried out for various periods within the range of 1 day to 5 days. Thereafter, dissociation and reaggregation of the obtained cells were carried out. That is, the cells were dissociated on Day 2 (d2), Day 2.25 (d2.25), Day 2.5 (d2.5), Day 2.75 (d2.75), Day 3 (d3), Day 3.25 (d3.25), Day 3.5 (d3.5), Day 3.75 (d3.75), Day 4.25 (d4.25), Day 4.5 (d4.5), Day 4.75 (d4.75), Day 5 (d5), or Day 6 (d6) after the induction, and subjected to the reaggregation culture.

In the last step, the cells were cultured under normal oxygen concentration for 8 days in STEMPRO 34 supplemented with 1% L-glutamine, 150 μg/mL transferrin, 50 μg/mL ascorbic acid, $3.9 \times 10^{-3}$% MTG, 10 ng/mL VEGF, and 5 ng/mL bFGF, and evaluated based on the content of cTNT-positive cells.

Figure 3:
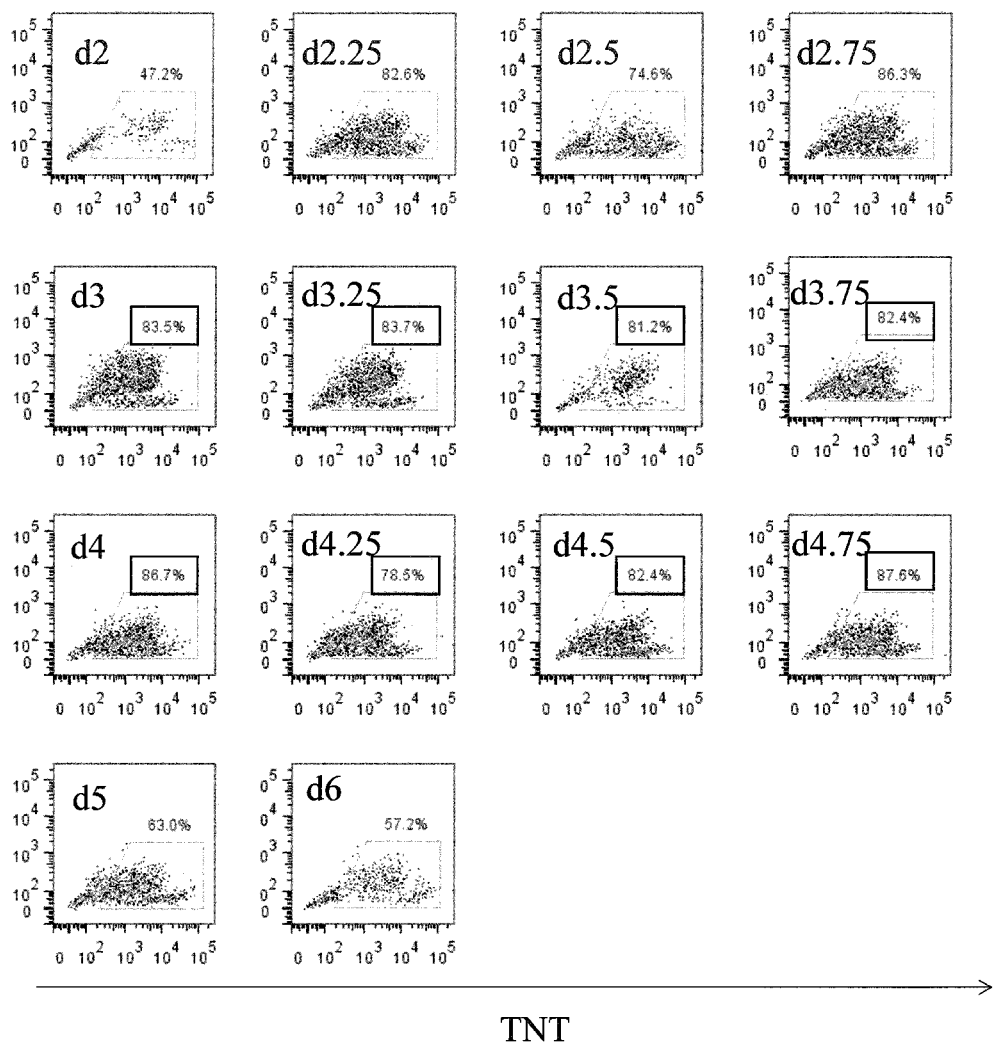
FIG. 3 shows the results obtained by the novel protocol in which the dissociation/reaggregation was carried out at various times between Day 2 (d2) and Day 6 (d6), wherein the content of TNT-positive cells among cells induced from iPS cells (201B7) (on Day 20 after the differentiation induction) was evaluated by flow cytometry.
Figure 4:
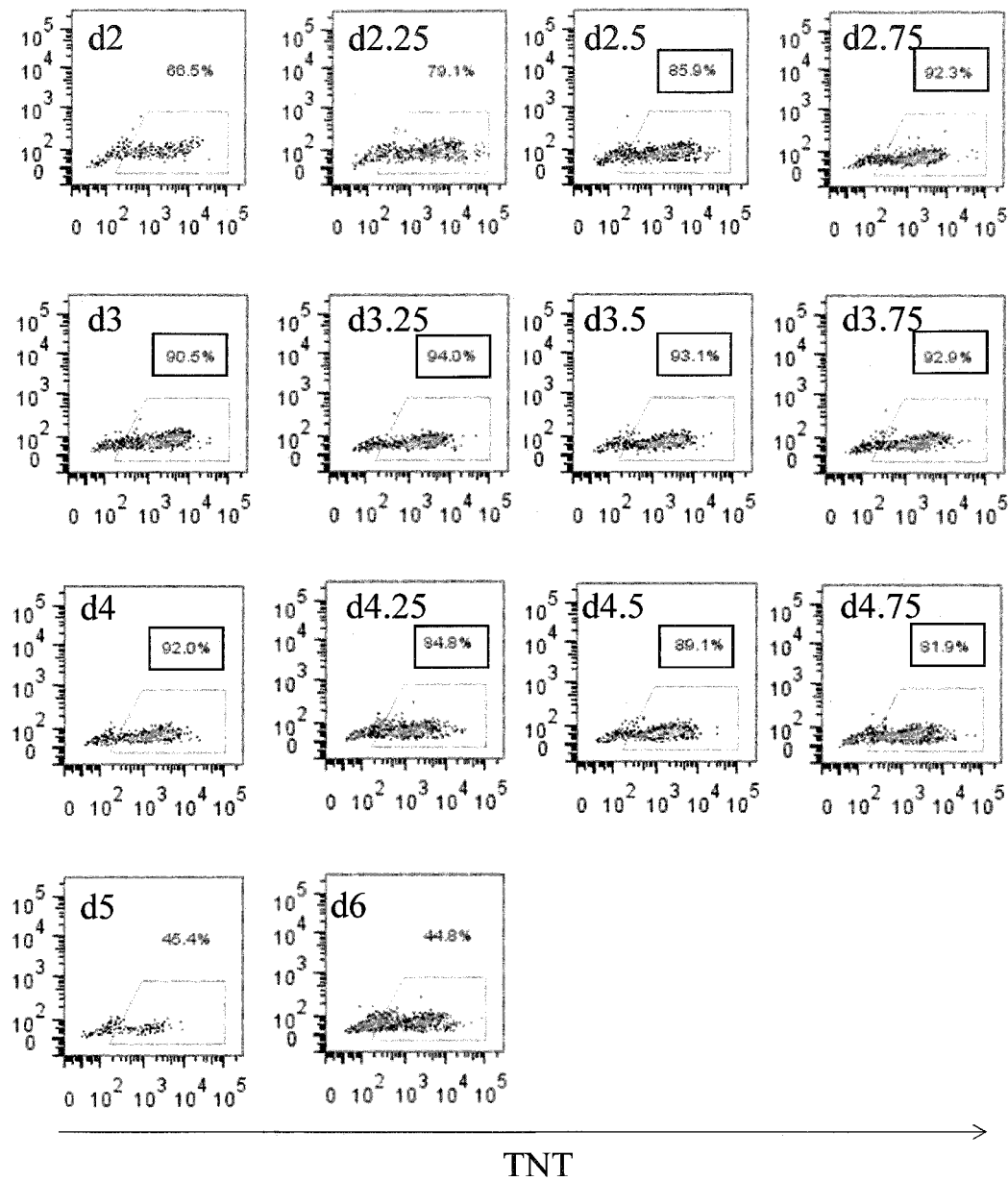
FIG. 4 shows the results obtained by the novel protocol in which the dissociation/reaggregation was carried out at various times between Day 2 (d2) and Day 6 (d6), wherein the content of TNT-positive cells among cells induced from ES cells (KhES1) (on Day 20 after the differentiation induction) was evaluated by flow cytometry.
Figure 5:
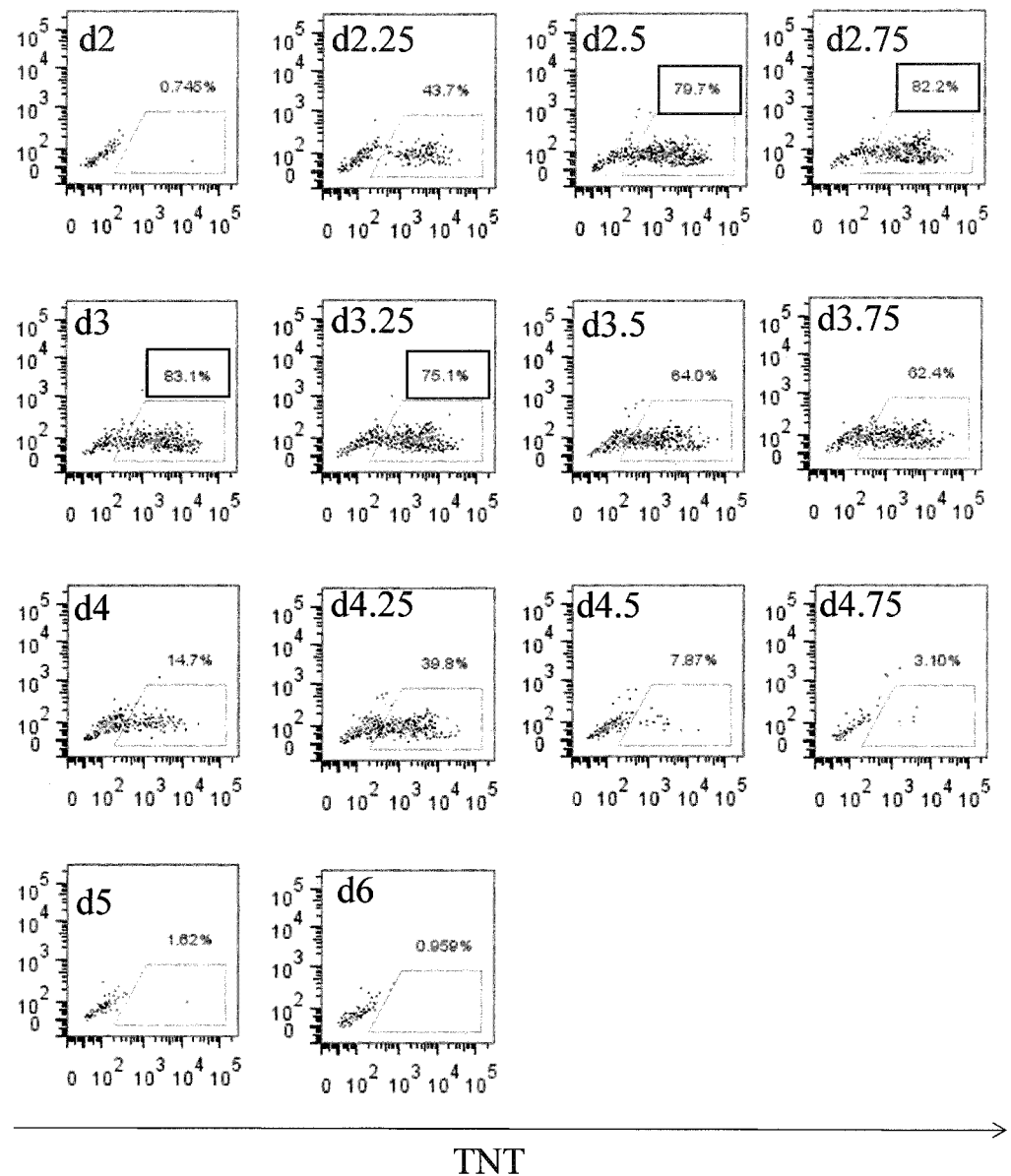
FIG. 5 shows the results obtained by the novel protocol in which the dissociation/reaggregation was carried out at various times between Day 2 (d2) and Day 6 (d6), wherein the content of TNT-positive cells among cells induced from iPS cells (610B1) (on Day 20 after the differentiation induction) was evaluated by flow cytometry.
Figure 6:
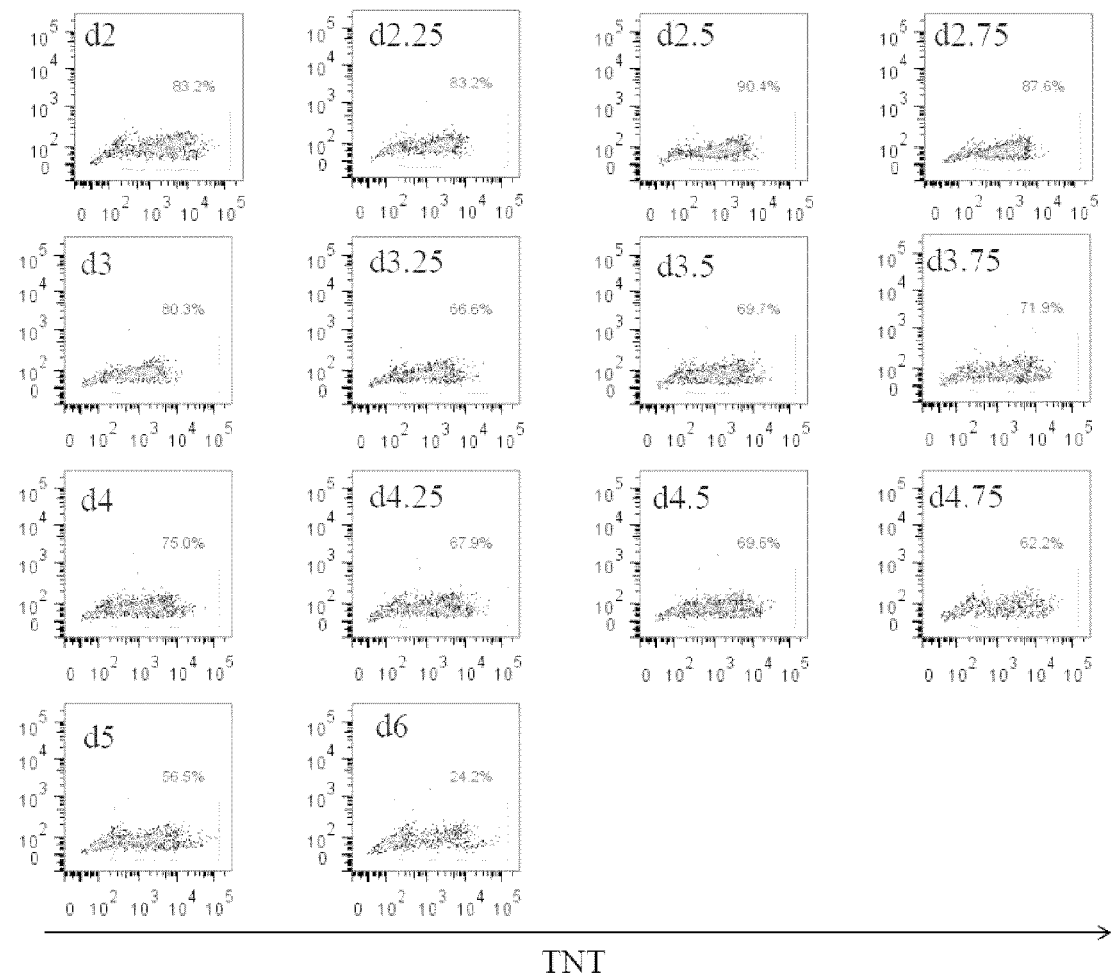
FIG. 6 shows the results obtained by the novel protocol (IW) in which the dissociation/reaggregation was carried out at various times between Day 2 (d2) and Day 6 (d6), wherein the content of TNT-positive cells among cells induced from iPS cells (409B2-2) was evaluated by flow cytometry.

As a result, in the cases of the 201B7 cell line, it was found that, when the cells were dissociated between Day 3 (d3) and Day 4.75 (d4.75) after the induction, and then subjected to the reaggregation culture, the content of cardiomyocytes was as high as 78.5% to 87.6% (FIG. 3). Similarly, in the cases of the KhES1 cell line, the dissociation of the cells between Day 2.5 (d2.5) and Day 4.75 (d4.75) followed by the reaggregation culture resulted in contents of cardiomyocytes of 81.9% to 94.0% (FIG. 4), and, in the cases of the 610B1 cell line, the dissociation of the cells between Day 2.5 (d2.5) and Day 3.25 (d3.25) followed by the reaggregation resulted in contents of cardiomyocytes of 75.1% to 83.1% (FIG. 5). In the cases of the 409B2-2 cell line, the dissociation of the cells between Day 2 (d2) and Day 3 (d3) followed by the reaggregation resulted in contents of cardiomyocytes of 80.3% to 90.4% (FIG. 6).

Then, differentiation induction of the 409B2-2 cell line was carried out in the same manner as in the modified method for inducing cardiomyocytes described above except for the culture step after the operation of dissociation (hereinafter referred to as the IWDS method). The culture step after the operation of dissociation in the IWDS method was as follows.

(Day 2 to Day 6) After the operation of dissociation, the medium was removed, and culture was carried out for 4 days at 37° C. under 5% oxygen in STEMPRO 34 supplemented with 1% L-glutamine, 150 μg/mL transferrin, 50 μg/mL ascorbic acid, $3.9 \times 10^{-3}$% MTG, 10 ng/mL VEGF (R&D), 1 μM IWP-3 (Stemolecule), 600 nM Dorsomorphin, and 5.4 μM SB431542.

Figure 7:
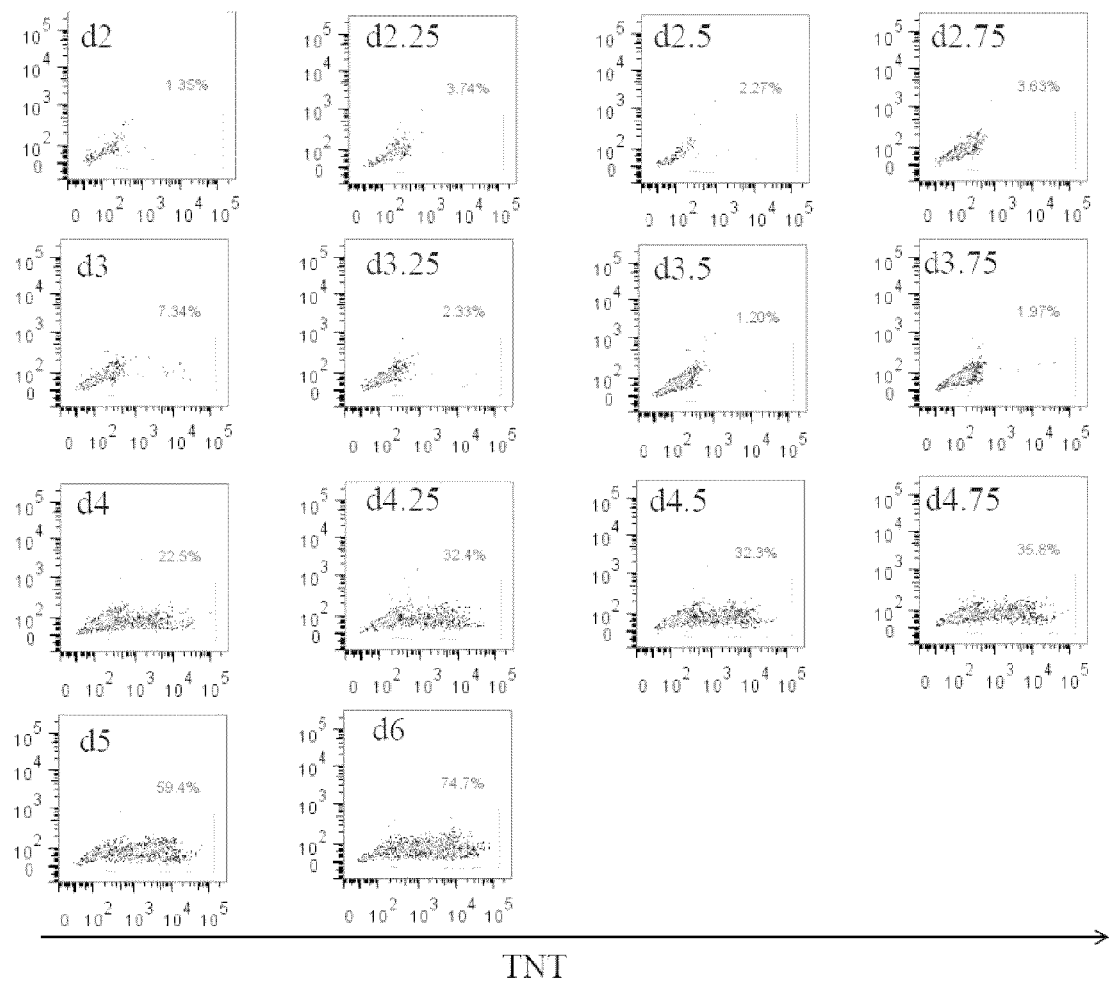
FIG. 7 shows the results obtained by the novel protocol in which Dorsomorphin and SB431542 were added (IWDS) and the dissociation/reaggregation was carried out at various times between Day 2 (d2) and Day 6 (d6), wherein the content of TNT-positive cells among cells induced from iPS cells (409B2-2) was evaluated by flow cytometry.

As a result, in the cases of the 409B2-2 cell line, it was found that, when the cells were dissociated between Day 5 (d5) and Day 6 (d6) after the induction, and then subjected to the reaggregation culture, the content of cardiomyocytes was as high as 59.4% to 74.7% (FIG. 7).

From these results, it was shown that, by using the modified method for inducing cardiomyocytes (IW) or the IWDS method described above, and dissociating the cells into single cells at a timing between Day 2 (d2) after the induction and Day 6 (d6) after the induction, followed by carrying out reaggregation culture, cardiomyocytes can be obtained more efficiently.

It was also shown that the present method does not require preliminary plating of cells on a Matrigel-coated surface, and enables simple and efficient induction of cardiomyocytes by dissociating the cells into single cells and allowing formation of EB cells with a definite number of cells. Thus, the present method was suggested to be a very useful method.

Example 3

Study of Timing of Dissociation/Reaggregation of EBs (2)

Figure 8:
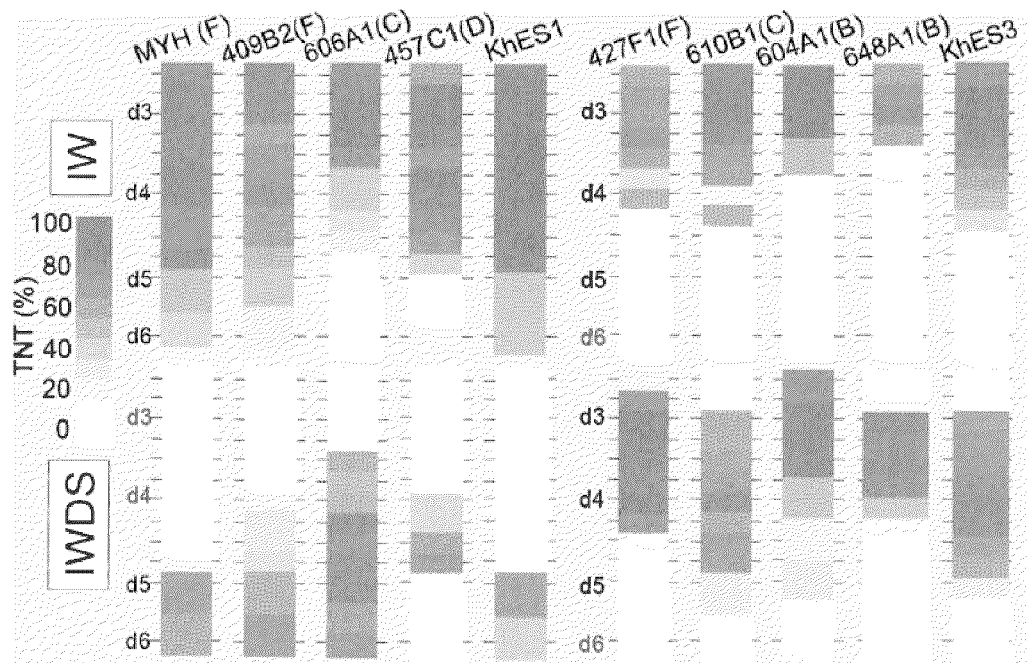
FIG. 8 shows the results obtained by the novel protocol (IW), or the novel protocol in which Dorsomorphin and SB431542 were added (IWDS), wherein the dissociation/ reaggregation was carried out at various times between Day 2.5 (d2.5) and Day 6 (d6) at intervals of 6 hours, and the contents of TNT-positive cells among cells induced from various types of iPS cells and ES cells were evaluated by flow cytometry. The iPS-derived cells used were MYH, 409B2, and 427F1, which are derived from fibroblasts; 606A1 and 610B1, which are derived from umbilical cord blood; 457C1, which is derived from dental pulp; and 604A1 and 648A1, which are derived from blood cells.

In the modified method for inducing cardiomyocytes (IW) and the IWDS method described above, the timing of the dissociation into single cells and the reaggregation carried out on Day 4 was changed to investigate the effect of the change on pluripotent stem cell lines (KhES1 cell line, KhES3 cell line, MYH cell line, 409B2 cell line, 427F1 cell line, 606A1 cell line, 610B1 cell line, 457C1 cell line, 604A1 cell line, and 648A1 cell line) (FIG. 8). The culture from Day 1 in STEMPRO 34 supplemented with 1% L-glutamine, 150 μg/mL transferrin, 50 μg/mL ascorbic acid, $3.9 \times 10^{-3}$% MTG, 18 ng/mL BMP4, 10 ng/mL bFGF, and 12 ng/mL activin A was carried out for various periods within the range of 1.5 days to 5 days. Thereafter, dissociation and reaggregation of the obtained cells were carried out. That is, dissociation of each cell line was carried out at various times between Day 2.5 (d2.5) and Day 6 (d6) after the induction at intervals of 6 hours, followed by reaggregation culture.

In the last step, the cells of each cell line were cultured under normal oxygen concentration until d15 in STEMPRO 34 supplemented with 1% L-glutamine, 150 μg/mL transferrin, 50 μg/mL ascorbic acid, $3.9 \times 10^{-3}$% MTG, 10 ng/mL VEGF, and 5 ng/mL bFGF, and evaluated based on the content of cTNT-positive cells.

As a result, the MYH cell line, 409B2 cell line, 606A1 cell line, 457C1 cell line, and KhES1 cell line subjected to the IW method showed high efficiency irrespective of when the dissociation was carried out followed by the reaggregation culture, during almost the entire process (d2.5 to d5). These cell lines subjected to the IWDS method showed high efficiency when the dissociation was carried out at a timing between the middle stage and a relatively late stage (d3.5 to d6), followed by the reaggregation culture (FIG. 8). On the other hand, the 427F1 cell line, 610B1 cell line, 604A1 cell line, 648A1 cell line, and KhES3 cell line subjected to the IW method showed high efficiency when the dissociation was carried out in a relatively early stage (d2.5 to d4), followed by the reaggregation culture. These cell lines subjected to the IWDS method showed high efficiency when the dissociation was carried out at a timing between a relatively early stage and the middle stage (d2.5 to d4.75), followed by the reaggregation culture (FIG. 8).

From these results, it was shown that, by using the modified method for inducing cardiomyocytes (IW) or the IWDS method described above, and dissociating the cells into single cells at a timing between Day 2.5 (d2.5) and Day 6 (d6) after the induction, followed by carrying out reaggregation culture, cardiomyocytes can be obtained more efficiently.

What is claimed is:

1. A method for producing cardiomyocytes from pluripotent stem cells, said method comprising:
    (1) forming an embryoid body/bodies from pluripotent stem cells, wherein the number of pluripotent stem cells is 1000 to 4000;
    (2) culturing said embryoid body/bodies obtained in the step (1) in a medium containing activin A, BMP4, and bFGF;
    (3) dissociating said embryoid body/bodies obtained in the step (2); and
    (4) culturing the dissociated embryoid body/bodies obtained in step (3) in a suspension culture comprising VEGF and a Wnt inhibitor for a time sufficient for reaggregation, whereby a cardiomyocyte content of at least 59.4% in the culture is obtained.

2. The method according to claim 1, further comprising:
    (5) culturing said embryoid body/bodies obtained in step (4) in a medium containing VEGF and bFGF.

3. The method according to claim 2, wherein said embryoid body/bodies is/are cultured for not less than 12 days in step (5).

4. The method according to claim 2, wherein said culture is carried out under hypoxic conditions in steps (2), (4), and (5).

5. The method according to claim 1, wherein said embryoid body/bodies is/are cultured for 1 day to 5 days in step (2).

6. The method according to claim 1, wherein said time sufficient for reaggregation is not less than 4 days in step (4).

7. The method according to claim 1, wherein said Wnt inhibitor is IWP-3 or IWP-4.

8. The method according to claim 1, wherein said medium used in step (4) further contains a BMP inhibitor and/or a TGFβ inhibitor.

9. The method according to claim 8, wherein said BMP inhibitor is Dorsomorphin, and said TGFβ inhibitor is SB431542.

10. The method according to claim 1, wherein said cardiomyocytes are human cardiomyocytes.

11. The method according to claim 1, wherein said culture is carried out under hypoxic conditions in steps (2) and (4).

12. The method of claim 1, wherein the suspension culture is carried out in a culture vessel, wherein the surface of the culture vessel is not treated with any coating selected from the group consisting of Matrigel®, collagen, gelatin, laminin, heparan sulfate proteoglycan, entactin, and polyhydroxyethyl methacrylate.

13. The method of claim 1, wherein the cells do not comprise a vector comprising an MYH promoter.

* * * * *